(12) United States Patent
Hollander et al.

(10) Patent No.: US 11,033,355 B2
(45) Date of Patent: Jun. 15, 2021

(54) MOUNTING DEVICE FOR MEDICAL EQUIPMENT

(71) Applicant: Biosense Webster (Israel) Ltd., Yokneam (IL)

(72) Inventors: Ludwig Eliezer Hollander, Haifa (IL); Ron Moshkovich, Tel Aviv (IL); Wyatt Wilson Pugh, Benton, AR (US); Jay Thomas Lambert, Benton, LA (US); Jakob Koby Stern, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 289 days.

(21) Appl. No.: 16/237,002

(22) Filed: Dec. 31, 2018

(65) Prior Publication Data
US 2020/0205933 A1 Jul. 2, 2020

(51) Int. Cl.
| F16M 11/00 | (2006.01) |
| A61B 90/57 | (2016.01) |
| A61G 13/10 | (2006.01) |
| F16B 2/02 | (2006.01) |

(52) U.S. Cl.
CPC ............ *A61B 90/57* (2016.02); *A61G 13/101* (2013.01); *A61B 2090/571* (2016.02); *A61G 2203/80* (2013.01); *F16B 2/02* (2013.01)

(58) Field of Classification Search
CPC ...... F16B 2/18; F16B 2/12; F16B 2/10; F16B 2/185; Y10T 29/53; A61G 7/05
See application file for complete search history.

(56) References Cited

U.S. PATENT DOCUMENTS

| 3,616,497 | A | | 11/1971 | Esposito, Jr. | |
| 5,108,213 | A | | 4/1992 | Shields | |
| 5,582,379 | A | * | 12/1996 | Keselman | A61F 5/3761 |
| | | | | | 248/229.25 |
| 8,499,484 | B2 | * | 8/2013 | Schneider | F41G 11/003 |
| | | | | | 42/124 |
| 2010/0109223 | A1 | * | 5/2010 | Mills | B25B 5/04 |
| | | | | | 269/207 |
| 2010/0117281 | A1 | | 5/2010 | Doyle | |
| 2014/0007408 | A1 | | 1/2014 | Nool | |

(Continued)

FOREIGN PATENT DOCUMENTS

DE 10 2013 108 574 B4 6/2017

OTHER PUBLICATIONS

Allen Medical 2019 Catalog, "General," 2018, pp. 97-113, Allen Medical Systems Inc., Acton, MA.
(Continued)

*Primary Examiner* — Amy J. Sterling
(74) *Attorney, Agent, or Firm* — Volpe Koenig (57) ABSTRACT

A medical equipment mounting device, for example a patch unit holder, is provided for holding medical equipment on a fixed structure. The mounting device includes a housing, a knob, and a locking ledge. The housing has an opening to receive and mount to a fixed structure. The knob has a ramp for defining a height of the locking ledge and functions as a push-button to cause the locking ledge to engage or release the fixed structure. The ramp of the knob is shaped to provide multiple discrete heights for the locking ledge. This configuration allows for the mounting device to be universal in mounting to various fixed structures, particularly various bedrail sizes.

12 Claims, 8 Drawing Sheets

(56) References Cited

U.S. PATENT DOCUMENTS

2014/0205371 A1    7/2014   Bally
2016/0136028 A1    5/2016   Koch et al.
2016/0361219 A1*   12/2016   Herrig ..................... F16B 2/12

OTHER PUBLICATIONS

Extended European Search Report dated May 4, 2020 for the European Patent Application No. 19220250.5.

* cited by examiner

MOUNTING DEVICE FOR MEDICAL EQUIPMENT

BACKGROUND

A variety of medical equipment, such as a patch unit, is utilized during a medical procedure. Complicated surgeries such as catheter ablation combine multiple procedures and require several instruments and monitors. For instance, a catheter ablation or diagnostic procedure can be aided by a real-time mapping and visualization system. Advanced Catheter Location (ACL) technology utilizes surface patches on a patient's chest and back to measure low-current emissions from electrodes in each catheter, and a software program can then calculate the position of each electrode. With the location of each electrode known, the surgeon can more accurately conduct the procedure.

A patch unit is an electronic medical device that connects back and chest patches to other components of a surgical system, such as a Patient Interface Unit (PIU), for ACL purposes in a medical procedure. Preferably, the patch unit is not disturbed during a surgical procedure and does not obstruct other components or tasks. The patch unit may be placed or mounted out of the way in the operating room (OR), such as on the frame of the surgical bed, while remaining close enough to provide a wired connection between the patches and the PIU. However, during surgery or between procedures, it may become necessary to shift the patch unit position or remove the patch unit from the area of the surgical bed.

It would be beneficial to offer a holder for a patch unit that can securely hold the patch unit in a desired location, easily be moved, and not obstruct the patch unit or other parts of a surgical system.

SUMMARY

In one aspect, a mounting device for medical equipment is provided, including a housing, a locking ledge, and a knob movable within the housing. The locking ledge is configured to engage a fixed structure. The knob has a ramp for adjusting a height of the locking pin. The ramp has a plurality of steps that each define a discrete height of the locking pin.

In another aspect, a medical equipment kit is provided, including a mounting device, a patch unit, a first equipment holder, and a second equipment holder. The mounting device has a housing with a first receiver. The first equipment holder is sized to receive the patch unit and is mountable in the first receiver. The second equipment holder is mountable in a second receiver of the housing.

BRIEF DESCRIPTION OF THE DRAWINGS

The present invention is illustrated by way of example, and not by way of limitation, in the figures of the accompanying drawings in which.

DETAILED DESCRIPTION OF THE PREFERRED EMBODIMENTS

The present disclosure is directed to a mounting device for medical equipment. In the present embodiment as described herein, the mounting device 10 (also referred to as a patch unit holder 10) may be used in catheterization, such as cardiac catheterization. For purposes of explanation, the mounting device 10 will be described with reference to catheterization procedures with a patch unit 920 used for catheter location monitoring. However, those of skill in the art would realize that in other embodiments, the mounting device 10 may be used in conjunction with other surgical, therapeutic, or diagnostic procedures.

Figure 1:
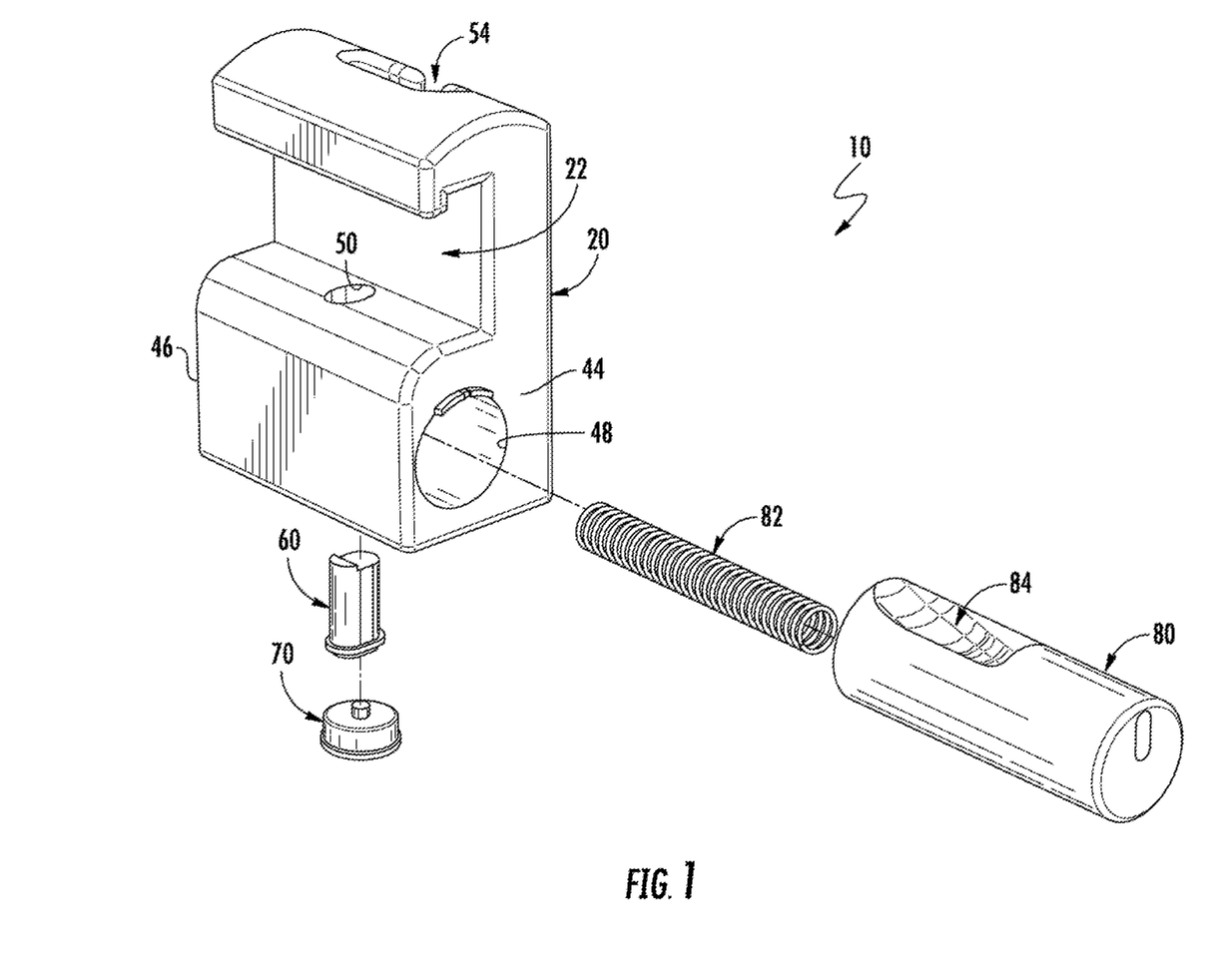
FIG. 1 is an exploded perspective view of a mounting device according to an embodiment of the present invention.

FIG. 1 shows an exploded view of a mounting device 10 in accordance with an embodiment of the present application, including a housing 20 with an opening 22, a locking ledge 60, a guide pin 70, and a knob 80 biased by a spring 82 and including a ramp 84. As discussed further below, the mounting device 10 may be used to mount to a fixed structure and may support one or more holders for equipment such as medical equipment.

Figure 2A:
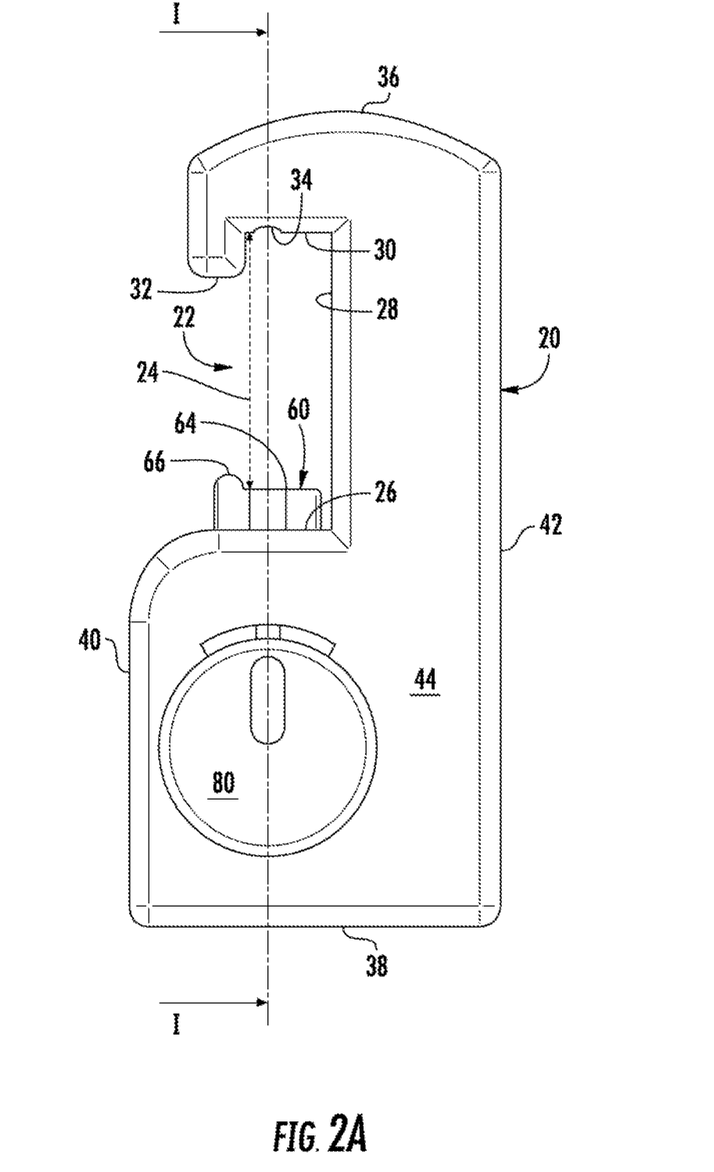
FIG. 2A is a side elevation view of a housing of the mounting device of FIG. 1.

The opening 22 of the housing 20, as best shown in FIG. 2A, has a height 24 that is adjustable via the locking pin 50 to accommodate and clamp to various sizes of a bedrail 800 (see FIG. 6A) or other fixed structure as further discussed below. The opening 22 is defined by at least a bottom 26, inner side 28, and a top side 30. A lip 32 may also be provided to partially enclose the open side of the opening 22 round the fixed structure. In this manner, the opening 22 is considered generally C-shaped. A depression 34 may be provided in the top side 30 to receive and positively engage a portion of the fixed structure.

Figure 2B:
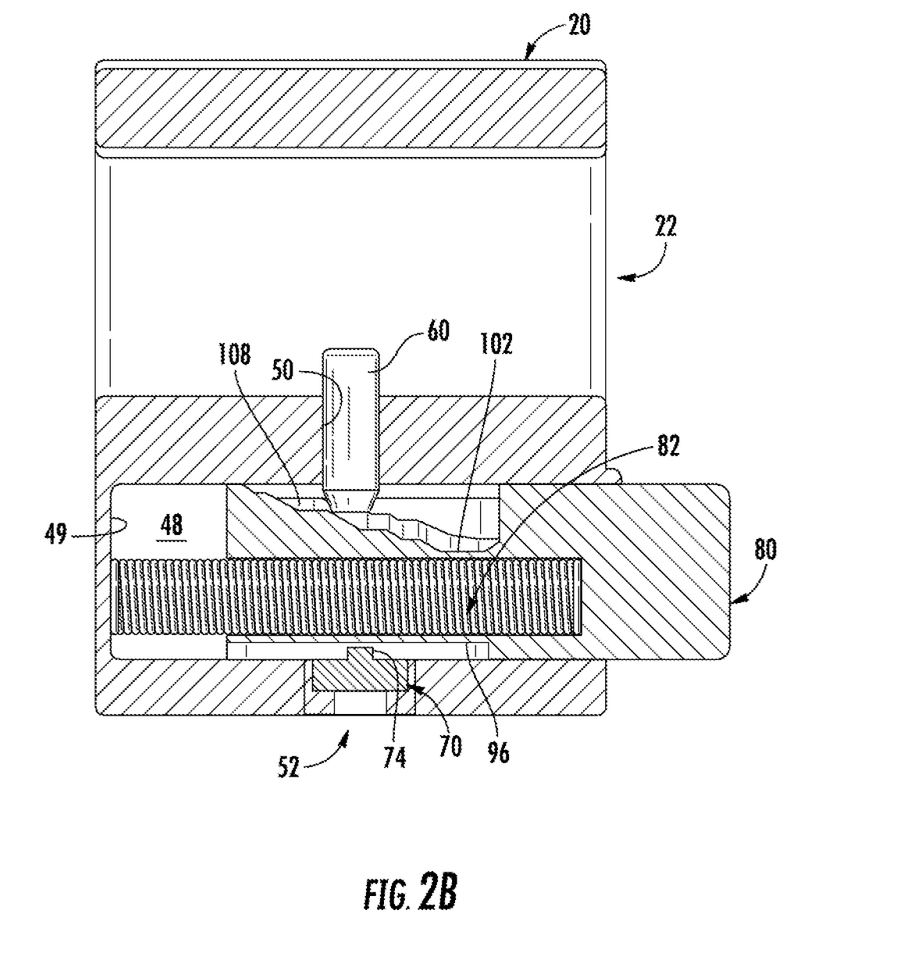
FIG. 2B is a cross-sectional view of the housing of FIG. 2A taken along the line I-I.
Figure 2C:
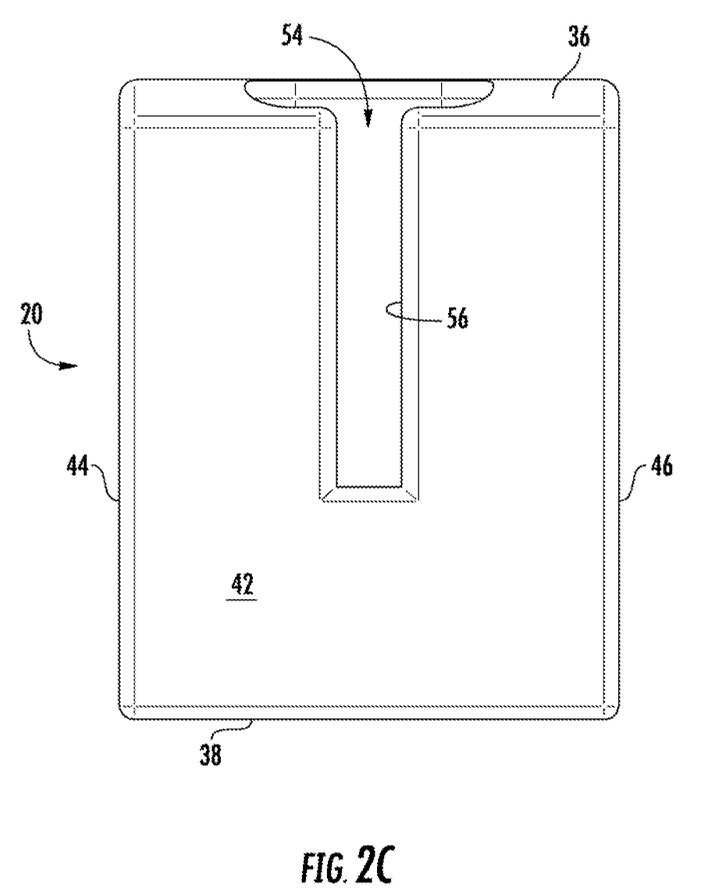
FIG. 2C is a rear elevation view of the housing of FIG. 2A.

The housing 20, shown in FIGS. 2A-2C, further includes a top 36, bottom 38, front 40, rear 42, and two sides 44, 46. The opening 22 is open toward the front 40 of the housing. A horizontal bore 48 is provided for receiving the knob 80 and the spring 82. In the illustrated embodiment, the bore 48 is formed in the first side 44 and extends substantially across the width of the housing 20 to a terminus 49 located proximate the second side 46. The bore 48 as illustrated extends parallel to and below the opening 22.

A primary vertical bore 50 is provided in the housing 20 for receiving the locking ledge 60 and connecting the horizontal bore 48 to the opening 22. A secondary vertical bore 52 is provided in the housing 20 for receiving the guide pin 70 and communicates with the horizontal bore 48. When assembled, the secondary vertical bore 52 also communicates with the guide slot 96 formed in the knob 80. As discussed below, this communication allows a catch 74 of the guide pin 70 to engage an end wall 98 of the knob 80. The secondary vertical bore 52 may also be used for installation of the locking ledge 60 prior to the knob 80 being installed in the horizontal bore 48.

As best shown in FIG. 2C, the rear 42 of the housing 20 includes a receiver 54, illustrated in the exemplary embodiment as a track or slot. The receiver 54 may be a T-shaped track and extends from the top 36 of the housing 20 toward the bottom 38, and may extend along more than half of the height of the back 42. The receiver 54 has an open end 56 extending along the back 42. In alternative embodiments, the open end 56 of the receiver 54 may extend along the top 36 or bottom 38 of the housing 20. In further alternatives, the receiver 54 may be replaced with other suitable receivers such as pin holes, threaded holes, clips, hooks, or the like.

Figure 3A:
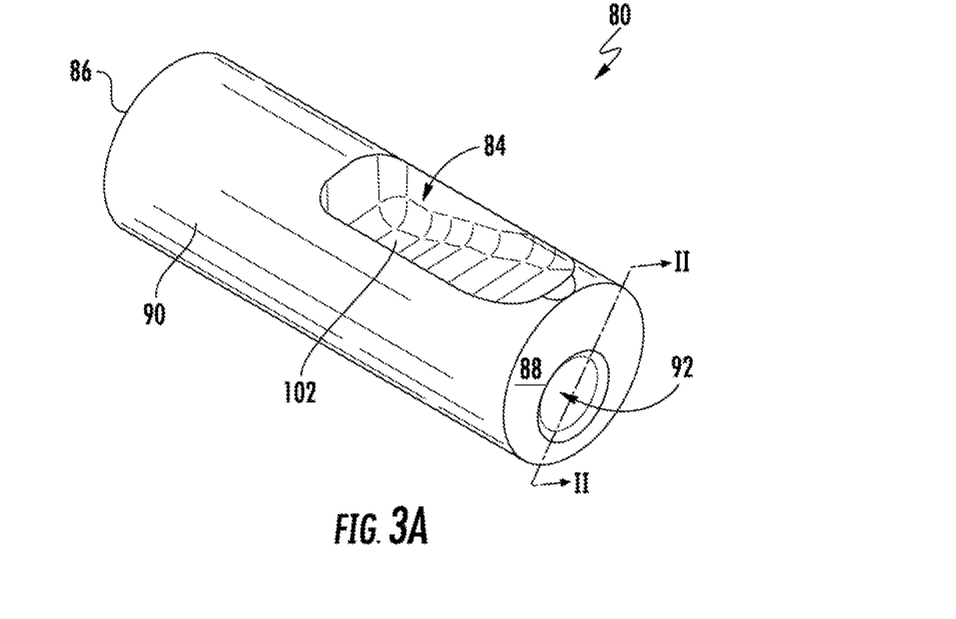
FIG. 3A is a top perspective view of a knob of the mounting device of FIG. 1.
Figure 3B:
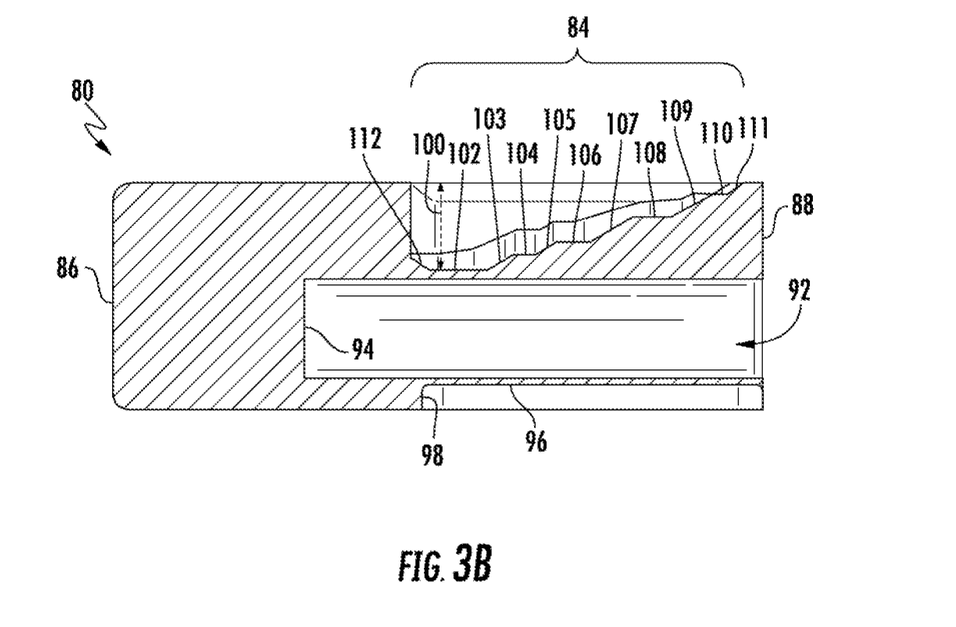
FIG. 3B is a cross-sectional side view of the knob of FIG. 3A taken along the line II-II.

Turning to FIGS. 3A and 3B, the knob 80 is shown including a first face 86, a second face 88, and a body 90. The knob 80 is illustrated as an elongate cylinder, although other elongate shapes are contemplated with cross-sections such as oval, square, or rectangle. The knob 80 and the bore 48 are correspondingly sized and shaped such that the knob may slide within the bore in a push-button fashion. The knob 80 further includes a spring slot 92, which terminates in an end wall 94, for receiving the spring 82.

The ramp 84 of the knob 80 includes a series of sloped sections and steps for changing the height of the locking ledge 60 to effectively adjusting the height 24 of the opening 22 of the housing 20. As such, the ramp 84 has a depth 100 that varies along the series of sloped sections and steps.

In particular, the ramp 84 may include a first step 102, a second step 104, a third step 106, a fourth step 108, and a fifth step 110. Each of the steps 102/104/106/108/110 is at a separate discrete depth 100. A series of sloped sections 103, 105, 107, and 109 are respectively interspersed between the steps. When assembled with the locking ledge 60, the head 68 of the locking edge can selectively move along the ramp 84, guided by the sloped sections 103/105/107/109 to a selected step 102/104/106/108/110. Terminal sloped sections 111 and 112 are also provided in the ramp 84 for retaining the head 68 in the ramp 84.

The knob 80 also includes a guide slot 96, which terminates in an end wall 98, for receiving the catch 74 of the guide pin 70. As illustrated in FIG. 4B, the guide slot 96 may have a longitudinal length corresponding to the first step 102 of the ramp 84, effectively limiting the longitudinal movement of the knob laterally away from the housing 20 as discussed further below.

The return spring 82 is mounted between the terminus 49 of the bore 48 of the housing 20 and the end wall 94 of the spring slot 92 of the knob 80. Although illustrated as a coil spring, various other spring types or resilient materials may be provided, including a rubber or elastomeric block. When assembled as shown in FIG. 2B, the return spring 82 pushes the knob 80 outward/rightward. As a result, the ramp 84 is pushed rightward, the depth 100 is effectively decreased, and the locking ledge 60 is pressed upward. Once the locking ledge 60 abuts the bedrail 800, it cannot move further upward, the knob 80 cannot move further outward/rightward, and the locking rest engages one of the steps 102/104/106/108/110.

Figure 4:
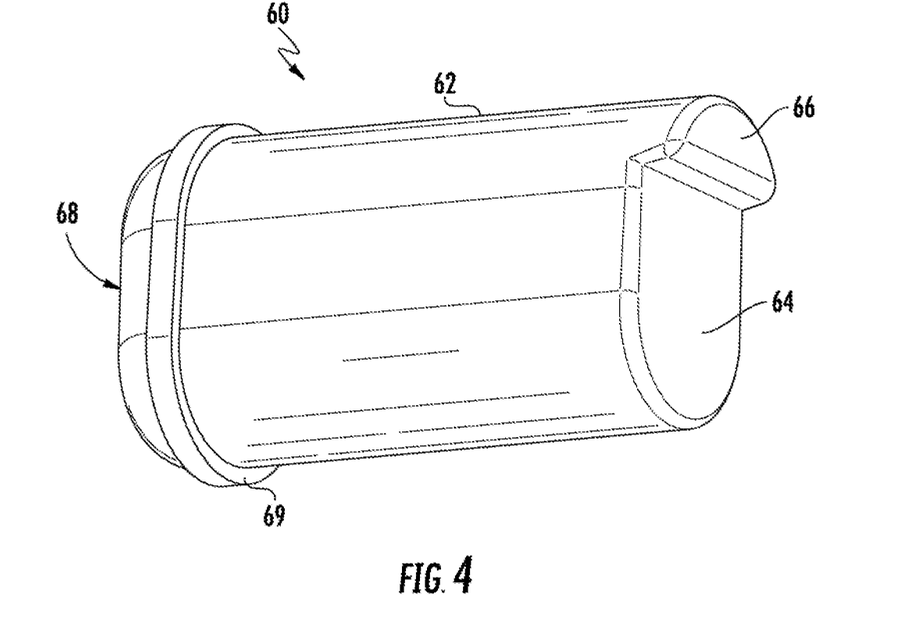
FIG. 4 is a side perspective view of a locking ledge of the mounting device of FIG. 1.

In FIG. 4, an exemplary locking ledge 60 is illustrated including a body, a top end 64, a hill 66, and a bottom 68. The body 62 is elongate with an oval cross section, although other cross-sectional shapes are contemplated, including round, rectangle, square, and the like. The body 62 is sized and shaped to slide within the primary vertical bore 50 of the housing 20. The top end 64 may be substantially flat and, when assembled, adjusts the effective height 24 of the opening 22 and engages the bedrail 800 or other fixed structure. The hill 66 extends from the top end 64 and is positioned opposite the inner side 28 of the opening 22. As such, similar to the lip 32 of the housing 20, the hill 66 may partially enclose the open side of the opening 22 around the fixed structure 800.

The bottom 68 of the locking ledge 60 may have a rim 69 around a perimeter of the bottom to serve as a catch on the housing 20 to prevent the locking ledge from sliding completely up and out of the primary vertical bore 50. When assembled, the bottom 68 engages the ramp 84 of the knob 80. To aid in adjustment along the ramp 84 and particularly along sloped sections 103/105/107/109, the bottom 68 may have rounded or beveled corners. The bottom 68 has a terminal face that may be substantially flat to rest on and engage a selected one of the steps 102/104/106/108/110 of the ramp 84.

In the illustrated embodiment, gravity acts upon the locking ledge 60 to force it toward the ramp 84, and gravity maintains engagement between the bottom 68 and the ramp 84 while the knob is moved. However, it is contemplated that additional structure such as springs may be provided to bias the locking ledge toward the ramp 84.

Figure 5:
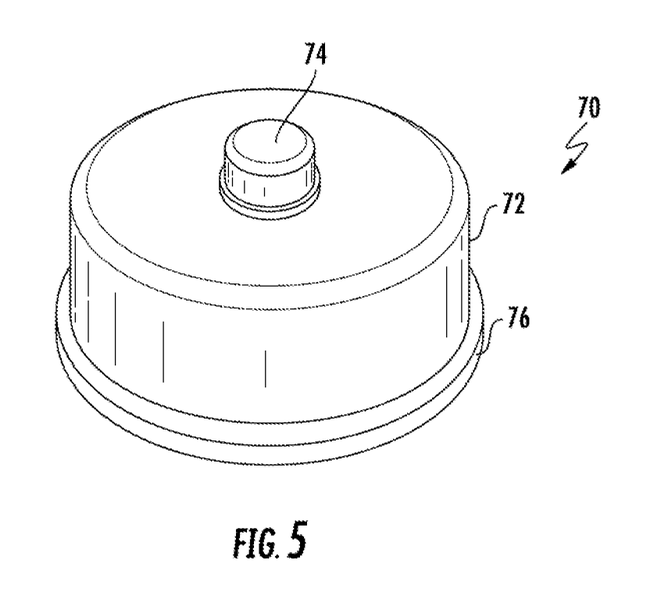
FIG. 5 is a top perspective view of a guide pin of the mounting device of FIG. 1.

In FIG. 5, an exemplary guide pin 70 is illustrated. The body 72 may fit into the secondary vertical bore 52 with a press fit, threading, positive engaging structure, or the like. The guide pin 70 includes a catch 74 extending axially therefrom. The catch 74 extends into the guide slot 96 of the knob 80. The catch 74 functions to prevent the knob 80 from rotating, which maintains the ramp 84 in an aligned position with the locking ledge 60. The catch 74 also functions to prevent the knob 80 from accidentally exiting the horizontal bore 48 of the housing 20, by engaging with the end wall 98.

In use, depressing the knob 80 (that is, inserting the knob further into the housing 20) increases the depth 100 of the ramp 84, which in turn lowers the locking ledge 60, which results in a larger height 24 of the opening 22 of the housing. Therefore, pressing the knob 80 allows the mounting device 10 to release from the bedrail 800 and/or accommodate a bedrail with a greater height (or diameter) 802. As noted above, beveled or rounded edges of the bottom 62 of the locking ledge 60 can aid in allowing the ramp 84 to move and in turn effect movement of the locking ledge. In the illustrated embodiment, the knob 80 is sized and positioned to be pressed with a user's thumb or single finger.

Figure 6A:
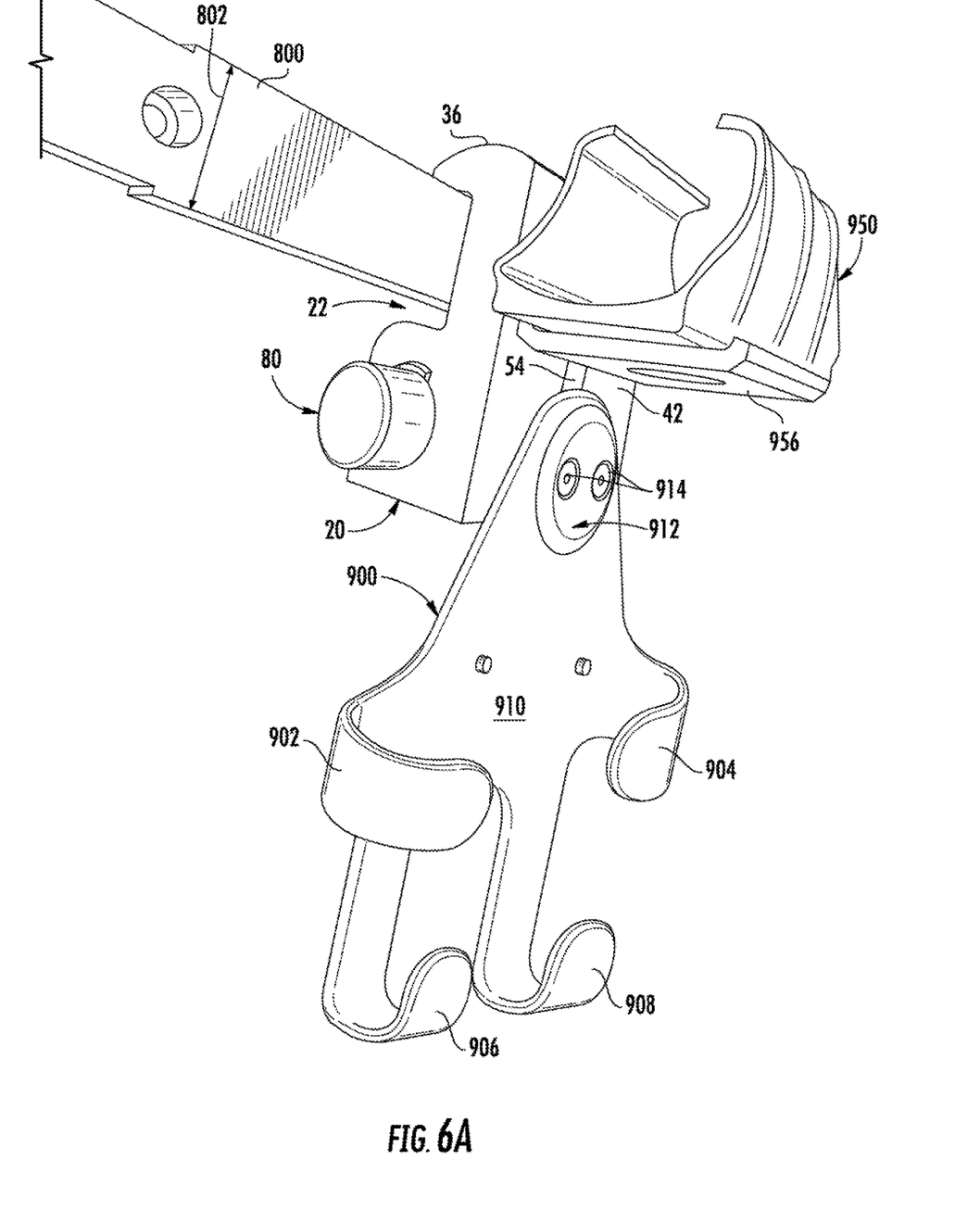
FIG. 6A is a perspective view of the mounting device of FIG. 1 with holders for medical equipment.
Figure 6B:
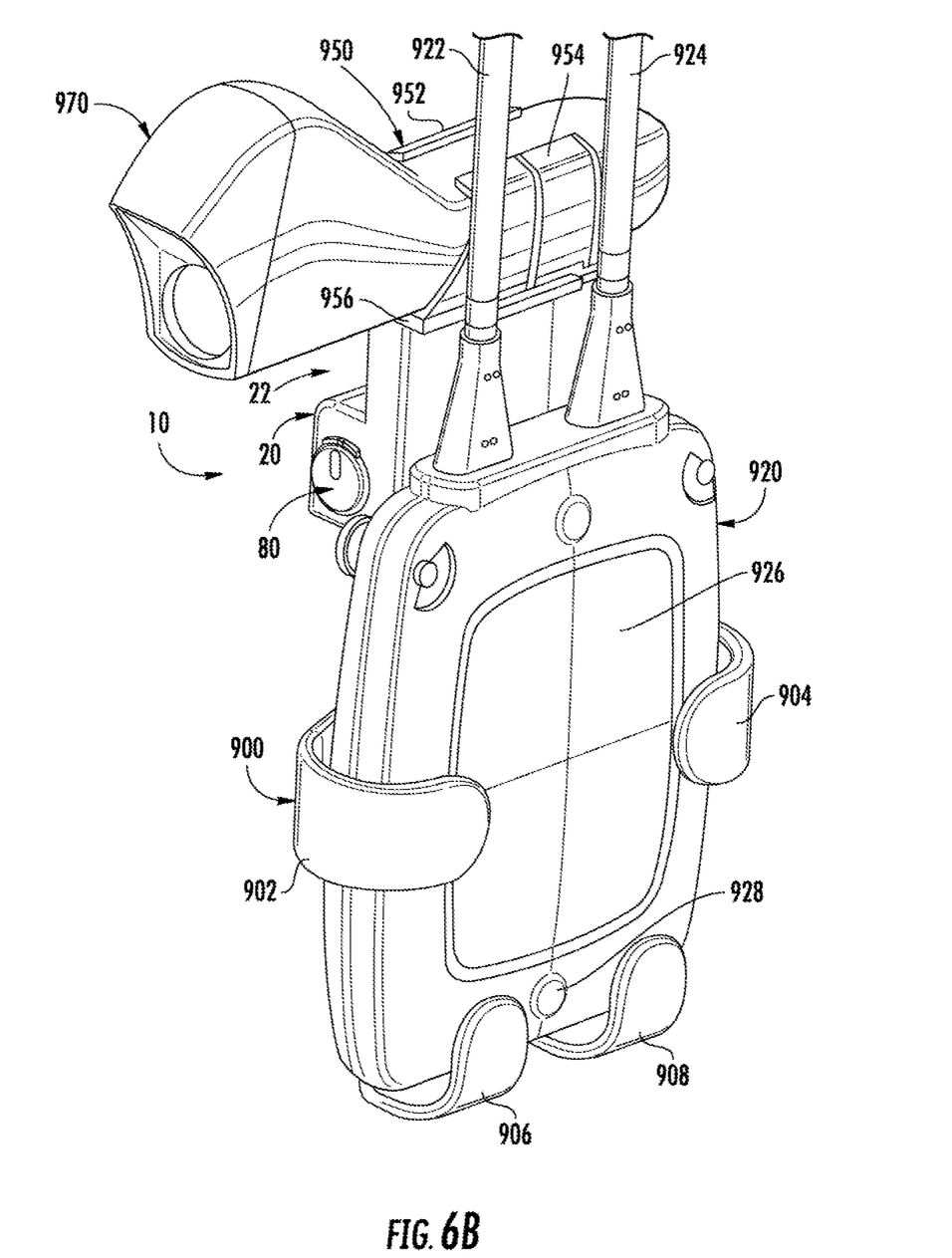
FIG. 6B is a perspective view of the mounting device of FIG. 6A holding a patch unit and a catheter unit.

As shown in FIGS. 6A-6B, the mounting device 10 may be mounted to a fixed structure such as a bed rail 800 and may support one or more holders, such as a first holder 900 and a second holder 950, for various devices such as medical equipment, for example a patch unit 920 and/or a catheter unit 970. One skilled in the art would appreciate that various other holders may be similarly attached to the mounting device 10 of the present application, as dictated by the user's needs and the intended device(s) to be held.

The exemplary first holder 900 includes first and second arms 902, 904 and first and second legs 906, 908 extending from a holder body 910. The arms 902, 904 and legs 906, 908 securely retain the patch unit 920 without obstructing any components thereof, such as wires 922 and 924 for connecting to patches, a display screen 926, and controls such as button 928. The first holder 900 has a mount 912 for engaging the housing 20, for example engaging at the receiver 54 of the housing 20. A pair of screws 914 may be provided to fixedly secure the mount 912 of the first holder 900 to the housing 20. In this manner, complementary threaded holes (not shown) for the screws 914 may be provided on the back 42 of the housing 20 and constitute a first receiver for the first holder 900 while the receiver 54 constitutes a second receiver for the second holder 950. In alternative embodiments, the first holder 900 may be held in the receiver 54 but with freedom to swing/pivot within the receiver 54.

The second holder 950 may also be removably mounted to the housing 20, for example engaging the receiver 54 and positioned above the first holder 900. The second holder 950 includes first and second arms 952, 954 extending from a base 956. The illustrated second holder 950 is configured to hold a catheter unit 970 (FIG. 2B), such as the QDot Catheter produced by Biosense Webster, Inc.

Table 1 below shows the height (or diameter) 802 of exemplary bedrails 800. The mounting device 10 of the present application may have an adjustable height 24 that accommodates some or all of these exemplary bedrail heights 802.

TABLE 1

Exemplary Dimensions of Bedrail 800

| Source | Type | Dimension 804 (inches) | Dimension 804 (mm) |
| --- | --- | --- | --- |
| U.S. Table | Side rails (O.R. tables) | ⅜" W × 1⅛" H | 9.525 mm × 28.575 mm |
| U.S. | Flat blade-style posts | ¼" W × 1" L | 25.4 mm × 6.35 mm |
| U.S. | Round | ⅝" (diameter) | 16 mm |
| U.S. | Rectangular | 1" × ⅜" | 25 mm × 9.5 mm |
| Europe | Rectangular | — | 10 mm × 25 mm |
| United Kingdom | Rectangular | — | 6.35 mm × 31.75 mm |
| Japan | Rectangular | — | 9 mm × 32 mm |
| Japan | Round | 0.6875" | 17.46 mm |
| Japan | Round | 0.625" | 15.87 mm |
| Japan | Round | 0.5" to 0.625" | 12.7 mm to 15.87 mm |

The present configuration allows a user (such as a surgeon, nurse, medical technician, or other practitioner) to mount or reposition the mounting device 10 onto the bedrail 800 (or other fixed structure) relatively quickly and easily. In particular, the mounting device 10 may be repositioned via one-handed operation. Moreover, manufacturing and inventory costs are reduced because the adjustability of the height 24 of the opening 22 may allow for a single mounting device 10 that has compatibility with a range of heights 802 of the bedrail 800. For example one embodiment of the mounting device 10 applicable to the present application may accommodate every standard bedrail size listed above in Table 1. One skilled in the art would recognize that a fixed depth of the opening 22 (defined by the bottom 26 and the top side 30) may be designed to accommodate a particular width or diameter of the bedrail 800.

It should be understood that many variations are possible based on the disclosure herein. Although features and elements are described above in particular combinations, each feature or element can be used alone without the other features and elements or in various combinations with or without other features and elements. For example, the horizontal bore 48, primary vertical bore 50, and secondary vertical bore 52 may be oriented at any angle relative to vertical/horizontal, so long as the primary vertical bore 50 allows gravity force the locking ledge 60 toward the ramp 84. The amount of steps 102/104/106/108/110 of the ramp 84 may vary, and generally an exemplary mounting device 10 applicable to the present invention may have a ramp 84 with two or more steps, at least three steps, at least four steps, at least five steps, at least six steps, at least seven steps, at least eight steps, at least nine steps, or at least ten steps. In view of Table 1, a ramp may have depths 100 for the steps 102/104/106/108/110 that encompass the minimum and maximum sizes listed, includes only U.S. sizes, includes only Japan sizes, or includes any combination of the listed sizes. Instead of the bedrail 800, the mounting device 10 may be mounted to various fixed structures such as the frame, arms, or legs of medical equipment; furniture; a counter; a table; or the like.

What is claimed is:

1. A mounting device for medical equipment, comprising:
    a housing;
    a locking ledge configured to engage a fixed structure;
    a knob movable within the housing, the knob including a ramp for adjusting a height of the locking pin, the ramp having a plurality of steps, wherein each step defines a discrete height of the locking pin,
    wherein the plurality of steps are substantially parallel.

2. The mounting device of claim 1, further comprising:
    a return spring biased against the knob to bias the locking ledge toward a closed position.

3. The mounting device of claim 1, wherein the plurality of steps are separated by angled sections of the ramp.

4. The mounting device of claim 1, wherein the housing includes a slot for receiving the fixed structure.

5. The mounting device of claim 4, wherein the locking ledge height adjusts to change an effective size of the slot of the housing.

6. The mounting device of claim 1, wherein the knob retracts within the housing to retract the locking ledge and release the fixed structure.

7. The mounting device of claim 6, further comprising:
    a return spring biasing the knob toward and an extended position and the locking ledge toward a closed position.

8. The mounting device of claim 6, wherein relative movement of the knob and the locking ledge is substantially perpendicular.

9. The mounting device of claim 1, wherein the housing includes a receiver configured to attach an equipment holder.

10. The mounting device of claim 9, wherein the receiver is a track, and the mounting device further comprises two equipment holders mounted in the receiver.

11. A medical equipment kit, comprising:
    a mounting device for medical equipment, including:
        a housing including a first receiver;
        a locking ledge configured to engage a fixed structure; and
        a knob movable within the housing, the knob including a ramp for adjusting a height of the locking pin, the ramp having a plurality of steps, wherein each step defines a discrete height of the locking pin,
    a patch unit;
    a first equipment holder sized to receive the patch unit and mountable in the first receiver; and
    a second equipment holder mountable in a second receiver,
    wherein the plurality of steps are substantially parallel.

12. The medical equipment kit of claim 11, further comprising a catheter,
    wherein the second equipment cradle is sized to receive the catheter.

* * * * *

UNITED STATES PATENT AND TRADEMARK OFFICE
CERTIFICATE OF CORRECTION

| | |
|---|---|
| PATENT NO. | : 11,033,355 B2 |
| APPLICATION NO. | : 16/237002 |
| DATED | : June 15, 2021 |
| INVENTOR(S) | : Ludwig Eliezer Hollander et al. |

It is certified that error appears in the above-identified patent and that said Letters Patent is hereby corrected as shown below:

In the Specification
In Column 2, Line 35, delete "locking pin 50" and insert -- locking ledge 60 --, therefor.
In Column 2, Line 52, delete "the" and insert -- to the --, therefor.
In Column 5, Line 62, delete "force" and insert -- to force --, therefor.

In the Claims
In Column 6, Line 36, in Claim 7, delete "and an" and insert -- an --, therefor.

Signed and Sealed this
Fifteenth Day of August, 2023

Katherine Kelly Vidal
*Director of the United States Patent and Trademark Office*